United States Patent [19]

Pierce et al.

[11] 4,062,853

[45] Dec. 13, 1977

[54] CHLORO-PYRIDINYLOXYMETHYL ESTERS OF THIOCYANIC ACID

[75] Inventors: James K. Pierce, Midland; Sharon S. Whipple, Sanford, both of Mich.

[73] Assignee: The Dow Chemical Company, Midland, Mich.

[21] Appl. No.: 381,942

[22] Filed: July 23, 1973

[51] Int. Cl.$^2$ .......................................... C07D 213/70
[52] U.S. Cl. ...................... 260/294.8 G; 260/294.8 E; 424/263
[58] Field of Search ................................ 260/294.8 G,

[56] References Cited

U.S. PATENT DOCUMENTS

| 3,711,486 | 1/1973 | Torba | 260/294.8 G |
| 3,758,482 | 9/1973 | Domenico | 260/294.8 G |

OTHER PUBLICATIONS

Templel et al., Rec. Trav. Chim. vol. 90 (2) pp. 97-104 (Feb. 1971)

Primary Examiner—Alan L. Rotman

Attorney, Agent, or Firm—Ted Post; C. Kenneth Bjork

[57] ABSTRACT

Chloro-pyridinyloxymethyl esters of thiocyanic acid of the formula

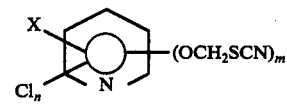

wherein $n$ is 1 to 4, $m$ is 1 to 3, X is H, F, CCl$_3$ or OCH$_2$Cl and the total number of substituent groups is no greater than 5. The compounds have fungicidal activity. The compounds are prepared by mixing a corresponding chloropyridine with sodium methoxide in methanol as reaction medium to form a corresponding chloro-methoxy pyridine, gradually adding to it sulfuryl chloride as a solution in carbon tetrachloride to form the corresponding chloromethoxy-chloropyridine and adding thereto potassium thiocyanate to form product chloropyridinyloxymethyl ester of thiocyanic acid.

8 Claims, No Drawings

CHLORO-PYRIDINYLOXYMETHYL ESTERS OF THIOCYANIC ACID

BACKGROUND OF THE INVENTION

No compounds having a close structural relationship to those claimed are known.

SUMMARY OF THE INVENTION

This invention concerns [(chloropyridinyl)oxy]-methyl esters of thiocyanic acid corresponding to the formula

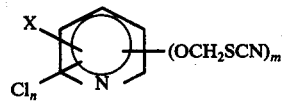

wherein $m$ represents an integer from 1, to 2, to 3, $n$ represents an integer from 1, to 2, to 3, to 4, and X represents H, F, $CCl_3$ or $OCH_2Cl$. Such compounds include, for example, [(3,5,6-trichloro-2-pyridinyl)oxy]methyl thiocyanate, [(2,3,5,6-tetrachloro-4-pyridinyl)oxy]methyl thiocyanate, [(2,3,5-trichloro-4-pyridinyl)oxy]methyl thiocyanate, [(3,5,6-trichloro-4-(chloromethoxy)-2-pyridinyl)oxy]methyl thiocyanate, [(3,5-dichloro-6-fluoro-2-pyridinyl)oxy]methyl thiocyanate and [(6-chloro-4-(trichloromethyl)-2-pyridinyl)-oxy]methyl thiocyanate.

The compounds are colorless crystalline solids or high boiling liquids which are insoluble in water and soluble in polar and non-polar solvents such as carbon tetrachloride, chloroform, acetone, methanol, ethanol, benzene, etc., and slightly soluble in hexane. The compounds have high fungicidal activity.

The compounds are prepared by mixing substantially equimolar proportions of a corresponding chloropyridine with an alkali metal methoxide, e.g., sodium or potassium methoxide in methanol as reaction medium, stirring the reaction medium at reflux for several hours, cooling the reaction medium and pouring it into ice water to precipitate the corresponding methoxy-chloropyridine. The latter is dissolved in a non-reactive solvent such as carbon tetrachloride and heated to reflux while gradually adding over a period of several hours sulfuryl chloride in solution in carbon tetrachloride. The reaction mixture is refluxed for a short time, cooled and the solvent evaporated in vacuum. The residue is a colorless liquid which when distilled through a fractionating Claisen head gives a pure fraction of the corresponding chloromethoxy-halopyridine. To a solution of the latter in a low-boiling polar solvent such as acetone or methanol is added in one portion a substantially equimolar amount of sodium or potassium thiocyanate. The resulting solution is stirred at reflux for several hours until reaction is substantially completed as followed by the formation of by-product sodium or potassium chloride. The reaction medium is then cooled, poured into ice water, the precipitate filtered off and dissolved in hot hexane or hexane-ether mixture containing 90% hexane and 10% ether. The resulting solution is dried over magnesium sulfate or other appropriate desiccant, filtered and cooled to approximately 0° C., whereupon the product crystallizes out and is recovered by filtration. The compounds are identified by elemental analysis, infra-red and nuclear magnetic resonance spectra.

DESCRIPTION OF THE PREFERRED EMBODIMENTS

The following example and teachings additionally describe a specific embodiment and the best mode contemplated by the inventors of carrying out the invention.

EXAMPLE: Preparation of [(3,5,6-trichloro-2-pyridinyl)-oxy]methyl thiocyanate

To a slurry of 97.5 g. (0.45 mole) 2,3,5,6-tetra-chloropyridine in 350 ml. anhydrous methanol add portionwise over a period of 10 minutes 24.3 g. (0.45 mole) sodium methoxide. The mixture is stirred at reflux for 2.5 hours, cooled, and poured into 1000 ml. ice water. The resulting precipitate is filtered, washed with 500 ml. water, and air dried to afford 92.2 g. (96%) colorless crystalline 2-methoxy-3,5,6-trichloropyridine, m.p. 52°–56° C.

To a solution of 92.2 g. (0.434 mole) 2-methoxy-3,5,6-trichloropyridine in 400 ml. carbon tetrachloride, which is illuminated and heated to reflux by a G.E. sunlamp, add dropwise over a period of 5 hours a solution of 58.6 g. (0.434 mole) sulfuryl chloride in 400 ml. carbon tetrachloride. The mixture is allowed to reflux for 1 hour, then is cooled and the solvent is evaporated in vacuum. The residue is a colorless liquid which is distilled through a 4-inch fractionating Claisen head to afford a pure fraction of 2-chloromethoxy-3,5,6-trichloropyridine, 52.5 g. (49%), b.p. 106°–110° C. at 1.3 mm. Hg.

To a solution of 24.7 g. (0.1 mole) 2-chloromethoxy-3,5,6-trichloropyridine in 200 ml. acetone add in one portion 10.7 g. (0.11 mole) potassium thiocyanate. The solution is stirred at reflux for 21 hours, cooled, and poured into 1600 ml. ice water. The resulting precipitate is filtered and dissolved in hot hexane. The hexane solution is dried over $MgSO_4$, filtered, and cooled to 0° C., whereupon the product cyrstallizes. Isolation by filtration affords 15.5 g. (57%) of [(3,5,6-trichloropyridinyl)oxy]methyl thiocyanate (I) as pale gold crystals, m.p. 94°–96° C.

Anal. Calcd. for $C_7H_3Cl_3N_2OS$: C, 31.19; H, 1.12; Cl, 39.46; N, 10.39; S, 11.86. Found: C, 31.43; H, 1.25; Cl, 39.2; N, 10.00; S, 12.20.

Pursuant to the procedure of the preceding example, substituting the corresponding halopyridine as starting material, the following compounds are prepared: Thiocyanic acid, [(2,3,5,6-tetrachloro-4-pyridinyl)oxy]-methyl ester, (II), m.p. 74°–75° C.

Anal. Calcd. for $C_7H_2Cl_4N_2OS$: C, 27.66; H, 0.66; Cl, 46.65; N, 9.21; S, 10.55. Found: C, 27.6; H, 0.85; Cl, 46.0; N, 9.41; S, 10.8.

Thiocyanic acid, [(2,3,5-trichloro-4-pyridinyl)oxy]-methyl ester, (III), m.p. 49°–52° C.

Anal. Calcd. for $C_7H_3Cl_3N_2OS$: C, 31.19; H, 1.22; Cl, 39.46; N, 10.39. Found: C, 31.2; H, 1.3; Cl, 41.6; N, 9.6.

Thiocyanic acid, [(3,5,6-trichloro-4-(chloromethoxy)-2-pyridinyl)oxy]methyl ester, (IV), m.p. 135°–146° C. Anal. Calcd. for $C_8H_4Cl_4N_2O_2S$: C, 28.77; H, 1.21; Cl, 42.46; N, 8.39. Found: C, 29.2; H, 1.2; Cl, 40.9; N, 8.70.

Thiocyanic acid, [(3,5-dichloro-6-fluoro-2-pyridinyl)oxy]methyl ester, (V), m.p. 78°–80° C.

Anal. Calcd. for $C_7H_3Cl_2FN_2OS$: C, 33.72; H, 1.19; Cl, 28.02; N, 11.07. Found: C, 33.91; H, 1.41; Cl, 28.0; N, 11.38.

Thiocyanic acid [(6-chloro-4-(trichloromethyl)-2-pyridinyl)-oxy]methyl ester, (VI), a colorless oil.

Anal. Calcd. for $C_8H_4Cl_4N_2OS$: C, 30.21; H, 1.27; N, 8.81; S, 10.08. Found: C, 30.2; H, 1.43; N, 8.62; S, 9.9.

The products of the invention are useful as antimicrobials for the control of fungi. This is not to suggest that the compounds of this invention and their mixtures are equally effective against all such organisms at the same concentration. For such uses the compounds or their mixtures can be employed in an unmodified form or dispersed on a finely divided solid and employed as dusts. Such mixtures can also be dispersed in water with the aid of a surface-active agent and the resulting emulsions employed as sprays. In other procedures, the products can be employed as active constituents in solvent solutions, oil-in-water or water-in-oil emulsions. The augmented compositions are adapted to be formulated as concentrates and subsequently diluted with additional liquid or solid adjuvant to produce the ultimate treating compositions. Good results are obtained when employing compositions containing fungicidal concentrations and usually from about 100 to about 1,000 parts by weight of one or more of the compounds per million parts of such compositions.

Incorporation of the compounds of this invention into materials which are subject to fungal attack inhibits the growth of the fungi and preserves the original value of the materials. The compounds are sufficiently non-volatile and water-insoluble that they will persist on or in such materials for long periods of time. Examples of materials which are adversely effected by fungal growth are latex and alkyd paint films, wood and wooden products. The inventive compounds are sufficiently active against fungi that only small quantities are required to prevent mildew on paint films or wood rot. The compounds are therefore useful for long-term protection against fungal growth in or on materials having a wood basis or a protective or decorative paint film subject to fungal attack.

In representative operations, the products of the invention when tested for fungicidal activity using conventional agar dilution tests gave complete growth inhibition against the following organisms at the indicated concentrations in parts per million:

| Fungus | Minimum Inhibitory Concentration, p.p.m. Compound | | | | | |
|---|---|---|---|---|---|---|
| | I | II | III | IV | V | VI |
| Candida albicans | 10 | >100 | 10 | 10 | 10 | 100 |
| Trichophyton mentagrophytes | 1 | 1 | 1 | 1 | 1 | 1 |
| Candida pelliculosa | 10 | >100 | 10 | 10 | 10 | 100 |
| Pullularia pullulans | 10 | 100 | 1 | 10 | 10 | 10 |
| Ceratocystis ips | 1 | 10 | 10 | 10 | 10 | 10 |
| Trichoderma sp. 42 | 10 | >100 | 10 | 10 | 10 | 100 |
| Aspergillus terreus | 1 | 10 | 1 | 10 | 1 | 1 |
| Rhizopus nigricans | 10 | >100 | 10 | 100 | 10 | 100 |

What is claimed is:

1. A chloro-pyridinyloxymethyl ester of thiocyanic acid corresponding to the formula

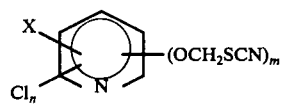

wherein $m$ represents an integer from 1 to 3, $n$ represents an integer from 1 to 4, X represents H, F, $CCl_3$ or $OCH_2Cl$, and the total number of substituent groups is no greater than 5.

2. A chloropyridinyloxymethyl ester of thiocyanic acid of the group consisting of [(3,5,6-trichloro-2-pyridinyl)-oxy]methyl thiocyanate, [(2,3,5,6-tetrachloro-4-pyridinyl)-oxy]methyl thiocyanate, [(2,3,5-trichloro-4-pyridinyl)oxy]-methyl thiocyanate, [(3,5,6-trichloro-4-(chloromethoxy)-2-pyridinyl)oxy]methyl thiocyanate, [(3,5-dichloro-6-fluoro-2-pyridinyl)oxy]methyl thiocyanate and [(6-chloro-4-(trichloromethyl)-2-pyridinyl)oxy]methyl thiocyanate.

3. The compound of claim 2 which is [(3,5,6-trichloro-2-pyridinyl)oxy]methyl thiocyanate.

4. The compound of claim 1 which [(2,3,5,6-tetrachloro-4-pyridinyl)oxy]methyl thiocyanate.

5. The compound of claim 1 which is [(2,3,5-trichloro-4-pyridinyl)oxy]methyl thiocyanate.

6. The compound of claim 1 which is [(3,5,6-trichloro-4-(chloromethoxy)-2-pyridinyl)oxy]methyl thiocyanate.

7. The compound of claim 1 which is [(3,5-dichloro-6-fluoro-2-pyridinyl)oxy]methyl thiocyanate.

8. The compound of claim 1 which is [(6-chloro-4-(trichloromethyl)-2-pyridinyl)oxy]methyl thiocyanate.

UNITED STATES PATENT AND TRADEMARK OFFICE
CERTIFICATE OF CORRECTION

PATENT NO. : 4,062,853
DATED : December 13, 1977
INVENTOR(S) : James K. Pierce and Sharon S. Whipple It is certified that error appears in the above-identified patent and that said Letters Patent are hereby corrected as shown below:

Column 2, line 40, "cyrstallizes." should read
-- crystallizes. --.

Column 4, delete lines 14 through 26; thus deleting Claim 1.

Column 4, line 27, Claim "2." should read -- 1. --.

Column 4, line 36, Claim "3." should read -- 2. -- and "of claim 2" should read -- of claim 1 --.

Column 4, line 38, Claim "4." should read -- 3. --; "of claim 1 which" should read -- of claim 1 which is --.

Column 4, lines 40, 42, 45 and 47, Claims "5.", "6.", "7." and "8." should read -- 4. --, -- 5. --, -- 6. -- and -- 7. -- respectively.

On the cover sheet "8 Claims" should read -- 7 Claims --.

Signed and Sealed this

Second Day of May 1978

[SEAL]

Attest:

RUTH C. MASON
Attesting Officer

LUTRELLE F. PARKER
Acting Commissioner of Patents and Trademarks